United States Patent
Mori

(10) Patent No.: US 11,260,098 B2
(45) Date of Patent: Mar. 1, 2022

(54) METHOD FOR SUPPRESSING OBESITY OR DEVELOPMENT OF OBESITY

(71) Applicant: Masatomo Mori, Midori (JP)

(72) Inventor: Masatomo Mori, Midori (JP)

(73) Assignee: Masatomo Mori, Midori (JP)

( * ) Notice: Subject to any disclaimer, the term of this patent is extended or adjusted under 35 U.S.C. 154(b) by 134 days.

(21) Appl. No.: 16/451,214

(22) Filed: Jun. 25, 2019

(65) Prior Publication Data

US 2019/0314439 A1    Oct. 17, 2019

Related U.S. Application Data

(60) Division of application No. 15/455,586, filed on Mar. 10, 2017, now abandoned, which is a continuation of application No. PCT/JP2015/004373, filed on Aug. 28, 2015.

(30) Foreign Application Priority Data

Sep. 10, 2014   (JP) .............................. JP2014-184432

(51) Int. Cl.
*A61K 36/746*   (2006.01)
*A23L 33/00*    (2016.01)
*A23L 33/105*   (2016.01)
*A61K 38/17*    (2006.01)

(52) U.S. Cl.
CPC .......... *A61K 36/746* (2013.01); *A23L 33/105* (2016.08); *A23L 33/30* (2016.08); *A61K 38/1709* (2013.01); *A23V 2002/00* (2013.01)

(58) Field of Classification Search
None
See application file for complete search history.

(56) References Cited

U.S. PATENT DOCUMENTS 7,795,390 B2 *  9/2010  Mori .................... A01K 67/027
                                                  530/350
2006/0088611 A1 *  4/2006  Wang .................... A61K 36/74
                                                  424/732

FOREIGN PATENT DOCUMENTS

CN      101057700 A     10/2007
JP      2009-62301 A    3/2009

OTHER PUBLICATIONS

International Search Report dated Dec. 1, 2015, in PCT/JP2015/004373, filed Aug. 28, 2015.
Nerurkar et al, "Regulation of glucose metabolism via hepatic forkhead transcription factor 1 (FoxO1) by Morinda citrifolia (noni) in high-fat diet-induced obese mice", British Journal of Nutrition, 2012, vol. 108, No. 2, pp. 218-228.

* cited by examiner

*Primary Examiner* — Susan Hoffman
(74) *Attorney, Agent, or Firm* — Oblon, McClelland, Maier & Neustadt, L.L.P.

(57) ABSTRACT

An appetite-suppressing composition is characterized by comprising, as an active component, the liquid component derived from Indian mulberry (*Morinda citrifolia*). The solution is the liquid component extracted from fermented Indian mulberry fruits, which includes the residual liquid containing the >3,000 component and the filtrated liquid containing the <3,000 component. Considerably, provided is the food that possesses the appetite-suppressing composition without showing the non-specific effect on appetite suppression.

2 Claims, 12 Drawing Sheets

METHOD FOR SUPPRESSING OBESITY OR DEVELOPMENT OF OBESITY

CROSS-REFERENCE TO RELATED APPLICATIONS

The present application is a divisional of U.S. patent application Ser. No. 15/455,586, filed Mar. 10, 2017, now abandoned, which is a continuation of International Application No. PCT/JP2015/004373, filed Aug. 28, 2015, which is based upon and claims the benefits of priority to Japanese Application No. 2014-184432, filed Sep. 10, 2014. The entire contents of these applications are incorporated herein by reference.

BACKGROUND OF THE INVENTION

Field of the Invention

The present findings show an appetite-suppressing composition. More specifically, the present invention is associated with an appetite-suppressing composition derived from a specific plant•fruit.

Discussion of the Background

Obesity is defined by overweight, which is obviously associated with high incidences of lifestyle-related disorders such as hyperglycemia, hypertension and hyperlipidemia. Japan Society for the Study of Obesity states that obesity is defined by 25 or more of body mass index (BMI), and that obesity disease is diagnosed by the case, in which obesity shows at least one health problem including hyperglycemia, hypertension, hyperlipidemia, fatty liver, a sleep apnea syndrome, hyperuricemia, a coronary artery disorder, a cerebrovascular disorder, a menstrual disorder, an orthopedic disorder, and obesity-related nephropathy. Obesity disease is also diagnosed by the other case, in which obesity shows a certain value or more of the visceral fat amount (Non-Patent Document 1). Furthermore, on the basis of obesity due to an increase in visceral fat, metabolic syndrome is diagnosed and significantly associated with cerebrovascular and cardiovascular disorders. Therefore, it is important that obesity disease and metabolic syndrome should be treated prior to development of severe health problems.

Body weight is maintained at a constant level by the mechanism of energy homeostasis, to which appetite and energy expenditure mainly contribute. Obesity is caused by dysregulation of energy homeostasis, i.e., increased appetite (overeating) over a long-period of time than energy expenditure. Appetite is mainly regulated by the hypothalamus in the brain, and it has recently become known that appetite is substantially regulated by active molecules, which are synthesized and secreted from peripheral adipocytes and affect on the brain hypothalamus.

In line of the regulation of appetite, the inventors of the present findings previously found nesfatin-1 as a molecule localized in the brain hypothalamus and adipocytes to suppress appetite and enhance energy expenditure. In the following studies, it have been revealed that nesfatin-1 suppressed differentiation and proliferation of adipocytes (Non-Patent Document 2).

On the other hand, among the pharmaceutical components of preparations that are clinically used at present, the approximately 30%-components are known to be derived from certain kinds of plants. Thus, when a component showing the same activity as nesfatin-1 contained in a plant and/or fruit, which may be commercially available as a food stuff or drinking material, its component is expected to show appetite suppression, resulting in improvement of obesity, from the aforementioned point of view. However, it remains unknown whether a liquid component extracted from plants and fruits shows the appetite-suppressing activity such as nesfatin-1.

Furthermore, even in the case, in which a liquid component derived from a certain kind of food product•fruit exhibits an activity of appetite suppression, it remains unknown as to whether the fractionation and isolation of the liquid component based on the molecular weight provides the stronger and longer activities of appetite suppression. In fact, although the liquid component derived from a fruit of Indian mulberry (Morinda citrifolia) contains some components showing the low molecular weight, it remains unclear whether these components exhibit appetite suppression. Furthermore, no determination has been made whether the components showing the high molecular weight exhibit the activity of appetite suppression (Non-Patent Document 3).

CITATION LIST

Non-Patent Document

Non-Patent Document 1: Contemporary clinical obesity, Summary of criteria for diagnosis of obesity: Nippon Rinsho 72: 13-18, 2014.

Non-Patent Document 2: Identification of nesfatin-1 as a satiety molecule in the hypothalamus: Nature 443: 709-712, 2006.

Non-Patent Document 3: Morinda citrifolia L. (Noni): a review of the scientific validation for its nutritional and therapeutic properties. Journal Diabetes and Endocrinology 3: 77-91, 2012.

SUMMARY OF THE INVENTION

Problem to be Solved by the Invention

The present invention is devised in view of the current states of the aforementioned techniques of a related art, and it is devised to provide an appetite-suppressing composition derived from a specific plant•fruit and to determine the effect of the composition.

Means for Solving Problem

The present invention devised to achieve the aforementioned purpose is related to the following [1] to [14].

[1] An appetite-suppressing composition characterized by containing a component derived from Indian mulberry (Morinda citrifolia) as an effective component.

[2] An appetite-suppressing composition characterized by being a liquid component derived from a fruit of Indian mulberry (Morinda citrifolia).

[3] The appetite-suppressing composition as described in [2], in which the liquid component derived from a fruit of Indian mulberry is a liquid component extracted from a fruit of Indian mulberry.

[4] The appetite-suppressing composition as described in [2] or [3], in which the liquid component derived from a fruit of Indian mulberry is a liquid component extracted from a fermented fruit of Indian mulberry.

[5] The appetite-suppressing composition as described in any one of [2] to [4], in which the liquid component derived from a fruit of Indian mulberry is a supernatant of a liquid component extracted from a fermented fruit of Indian mulberry.

[6] The appetite-suppressing composition as described in any one of [2] to [5], in which the molecular weight of constituents in the liquid component derived from a fruit of Indian mulberry is 3,000 daltons or more.

[7] The appetite-suppressing composition as described in [6], in which the constituents with a molecular weight of 3,000 daltons or more are a component containing a high amount of nesfatin-1, obtained by preparing the liquid component derived from a fruit of Indian mulberry using a molecular weight cut-off filter device.

[8] The appetite-suppressing composition as described in any one of [2] to [5], in which the molecular weight of constituents in the liquid component derived from a fruit of Indian mulberry is 3,000 daltons or less.

[9] The appetite-suppressing composition as described in [8], in which the constituents with a molecular weight of 3,000 daltons or less are a component with low molecular weight, whose component is obtained by preparing the liquid component derived from a fruit of Indian mulberry using a molecular weight cut-off filter device.

[10] The appetite-suppressing composition as described in [9], in which the constituents with a molecular weight of 3,000 daltons or less contain glutamic acid, asparaginic acid, arginine and alanine.

[11] The appetite-suppressing composition as described in any one of [2] to [5], which consists of a component with a molecular weight of 3,000 daltons or more containing a high amount of nesfatin-1 and a component with low molecular weight of 3,000 daltons or less, both of which are obtained by preparing the liquid component extracted from a fermented fruit of Indian mulberry using a molecular weight cut-off filter device.

[12] A food product which consists of or contains the appetite-suppressing composition as described in any one of [1] to [11].

[13] A method for suppressing obesity based on the administration of the appetite-suppressing composition as described in any one of [1] to [11].

[14] The appetite-suppressing composition as described in any one of [1] to [11] for suppressing the development of obesity.

Effect of the Invention

The present invention provides the appetite-suppressing composition with excellent effects that possess and/or consists of an effective liquid component derived from, for example, a fruit of Indian mulberry. The administration of the appetite-suppressing composition, as shown in the present invention, demonstrates a significant reduction of food intake, resulting in prevention and amelioration of obesity and health problems involving obesity disease and metabolic syndrome. Furthermore, the intake of the appetite-suppressing composition, as shown in the present invention, more easily induces dieting of obese human subjects.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
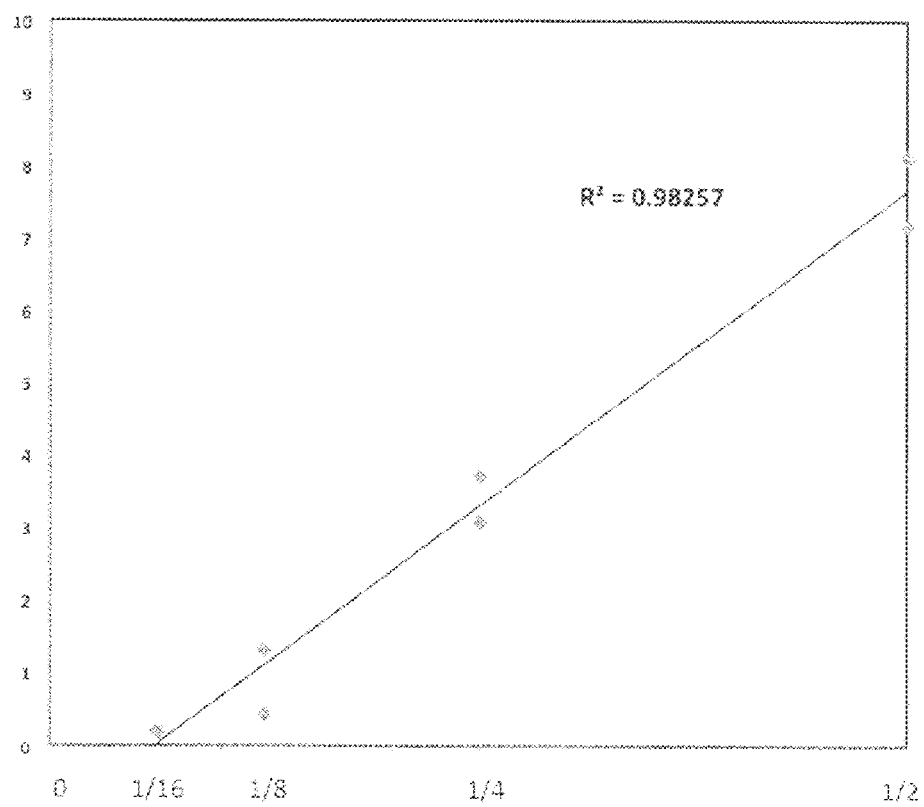
FIG. 1 shows the concentration dilution curve of the undiluted solution of liquid component of Indian mulberry, in which nesfatin-1 was detected by using the Nesfatin-1 ELISA kit.

The embodiments will now be described with reference to the accompanying drawings, wherein like reference numerals designate corresponding or identical elements throughout the various drawings.

Mode(S) for Carrying out the Invention

A novel molecule, which was found as a secretory protein showing expression in both brain hypothalamus and adipocytes, and activation by the peroxisome proliferator-activated receptor γ, i.e., a master regulator of metabolism, was named as nesfatin by the inventors of the present invention (Non-Patent Document 2). According to processing of nesfatin, nesfatin-1 and nesfatin-2/3 were generated. Nesfatin-1 was present in rat spinal fluids and human blood. When nesfatin-1 was centrally administered to the rat ventricle, food intake was significantly suppressed, resulting in reduction of body weight. In contrast, when the expression of nesfatin was decreased in the hypothalamus, food intake was elevated, leading to increases in body weight. Furthermore, the intracerebral administration of nesfatin-1 increased energy expenditure. On the other hand, nesfatin-2/3 did not exhibit the activity of appetite suppression or body weight reduction. Subsequent studies demonstrated that nesfatin suppressed proliferation of adipocytes and that the intraperitoneal administration of nesfatin-1 induced appetite suppression in a dose-dependent manner.

Meanwhile, in order to figure out a plant or a fruit, which contains a component exhibiting the same activity as nesfatin-1, the inventors of the present invention obtained liquid component and/or drinking water derived from plants and/or fruits, which are commercially available. By using the ELISA kit with high sensitivity and high specificity for nesfatin-1, considerable efforts were devoted to detect nesfatin-1 using these liquid components. Finally, it was found that the liquid component extracted from Indian mulberry (scientific name, Morinda citrifolia; general name, Indian mulberry) possessed nesfatin-1 and nesfatin-1-like molecules at a relatively high concentration. Accordingly, the undiluted solution of liquid component of Indian mulberry showed a significant suppression of food intake, whose suppression was not a non-specific effect.

It was also found that when the component obtained by fractionating the undiluted solution of liquid component of Indian mulberry was into two components of the residual liquid containing the >3,000 component and the filtrated liquid containing the <3,000 component, using the molecular weight cut-off filter device, the former component with containing the high amount of nesfatin-1 showed the enhanced activity of appetite suppression, and the latter component without containing most of nesfatin-1 showed the same activity of appetite suppression as the undiluted solution of liquid component.

Indian mulberry (Morinda citrifolia) is a small evergreen tree belonging to Rubiaceae, and it is known to be naturally found in part of Ryuku islands and Ogasawara islands in Japan.

In the present invention, as for the component derived from Indian mulberry, a liquid component may be mentioned. Preferred examples include a liquid component extracted from a fruit of Indian mulberry, in particular, an extract after fermenting the fruit for a suitable period, for example, 3 months or longer period.

The appetite-suppressing composition of the present invention shows, as an effective component, the aforementioned liquid component extracted from Indian mulberry, for example. It is also possible that the liquid component was prepared as a supernatant by means of centrifugation, or was fractionated to obtain the components showing the different molecular weights such as >3,000 daltons and <3,000 daltons, using the molecular weight cut-off filter device. It is also possible to adjust the concentration of these components using saline and buffer solutions. Furthermore, the examples as the forms and systems of administration, using the appetite-suppressing composition of the present invention, include an oral administration (employing a tablet, a capsule, a granule, a powder, a syrup, an enteric-dissolved preparation, a troche, or a drink preparation), a parenteral preparation like an injection solution, a suppository, a transdermally-absorbed preparation, and a preparation for outer application.

Furthermore, those formulations are prepared by using only the appetite-suppressing component of the present invention, or by appropriately combining its component with a certain vehicle (for example, saccharides such as sorbitol, glucose, lactose, dextrin, or starch, inorganic materials such as calcium carbonate, crystalline cellulose, saline, distilled water, sesame oil, corn oil, olive oil, safflower oil, and mixture of amino acids), a binder, a smoothing agent, an extender, a disintegrant, a surface active agent, a lubricant, a dispersant, a suspending agent, an emulsifying agent, a buffering agent, a preservative, a flavor, a fragrance, a coating agent, a carrier, a diluent, and an anti-oxidizing agent.

As the administration forms of the appetite-suppressing composition of the present invention, any form may be employed. Among them, the preferred form is the oral administration using an enteric-dissolved preparation, and the doses of oral administration are not particularly limited as long as the effect obtained. Furthermore, the amounts of intake•administration may vary depending on a health condition, body weight, sex, or age of subjects, and other factors. However, as a preparation for oral administration to adult human subjects, it is generally preferable in the present invention that the doses of administration are comparable to those of 600 mg to 3,600 mg (per kg of body weight) in terms of the amount of liquid component. Although the appetite-suppressing composition can be taken or administered depending on any intake administration schedule, it should be considered to be administered on several separated times per day, and its administration should be continued from several weeks to several months and more.

Furthermore, subjects taking the appetite-suppressing composition of the present invention are not particularly limited to subjects with obesity who require the composition. However, preferred are subjects with obesity who exhibit obesity disease and metabolic syndrome, subjects with obesity who tend to show health problems associated with obesity, mammals other than human subject who desire prevention and amelioration of lifestyle-related disorders, and subjects under dieting and physical exercise therapy for body slimming.

The administration of the appetite-suppressing composition of the present invention having the constitution, as described above, clearly showed appetite suppression. Particularly, the administration of the residual liquid containing the >3,000 component induced the enhanced appetite suppression with a long-period of efficiency. Thus, the appetite-suppressing composition of the present invention is also useful upon mixing with food products including a processed food, a health food and a health drink like a so-called food for specified health uses. Namely, examples of materials mixed with the appetite-suppressing composition of the present invention include a processed wheat-flour product represented by bread and noodles; a processed rice product like rice gruel, rice cooked with seasoned ingredients; snacks like biscuit, cake, jelly, chocolate, senbei (rice cracker), and ice cream; a processed soybean product such as tofu and processed tofu product; drinks such as a soft drink, a fruit juice drink, a vegetable drink, a squeezed liquid of mixed fruits, a squeezed liquid of mixed vegetables; a milk drink, and a carbonate drink; a dairy product such as yoghurt, cheese, butter, or milk; a seasoning such as soy sauce, sauce, miso, mayonnaise, or dressing; a meat or a processed meat product such as ham, bacon, or sausage; a processed sea food product such as hanpen (floated-type kamaboko), chikuwa (fish stick), fish can; a seasoning; and a fry oil. Furthermore, in addition to materials and/or substances as mentioned above, by blending with the appetite-suppressing composition of the present invention, an oral•enteric nutrition food product or a functional food product such as a tablet food like capsule, a concentrated fluid food, a natural fluid food, a semi-digested nutrition food, an elemental nutrition food, or a drink nutrition food can be produced.

Furthermore, examples of animal foods include a food for small animal like rabbit, rat, and mouse, and a pet food used for dog, cat, small bird, or squirrel.

Feeds and food products as various forms can be produced by suitably mixing the appetite-suppressing composition of the present invention with other food materials and/or substances including a solvent, a softening agent, an oil, an emulsifying agent, a preservative, a fragrance, a stabilizing agent, a coloring agent, an anti-oxidizing agent, a moisturizing agent, and a thickening agent.

EXAMPLES

Method

1. Food stuff or drink as materials: 22 kinds of liquids extracted from the plants•fruits as shown below, which are commercially available as food stuff and drink in public markets in the international street of Okinawa ken, were obtained. Each of liquid extracts was subjected to centrifuge at 1,500 rpm for 15 minutes to obtain a supernatant (this supernatant is described as the undiluted solution of liquid component). Twenty two materials were as follows;
1. Ukon (turmeric) tea 2. Mango squeeze 3. Dragon fruit squeeze 4. Shikusawa (Flat lemon) squeeze 5. Tankan squeeze 6. Sanpin (jasmine) tea 7. Tomato squeeze 8. Mugwort tea 9. Korean ginseng squeeze 10. Ulong tea 11. Green tea 12. Acerola squeeze 13. Lienu squeeze 14. Hab snake liquor 15. Island banana squeeze 16. Passion fruit squeeze 17. Snack pine squeeze 18. Papaya squeeze 19. Guava squeeze 20. Apple squeeze 21. Peach pine squeeze 22. Indian mulberry squeeze 2. Measurement: Using a human nesfatin-1 ELISA kit (manufactured by SHIBAYAGI Co., Ltd.) that was a sandwich-type system showing high sensitivity and high specificity for nesfatin-1, nesfatin-1 was measured in each of the undiluted solutions of liquid component. In the case of the liquid component, in which nesfatin-1 can be measured, the concentrations of leptin and adiponectin, all of which are involved in the appetite regulation in the brain hypothalamus and are present in human blood and adipocytes, were particularly measured by using an ELISA kit specific to each molecule, according to the methods manufactured by Mercodia.

3. Appetite-suppressing effect-1: In order to determine the appetite-suppressing effect of the liquid component, male mice with body weight of around 25 g were used. The undiluted solution of liquid component obtained as mentioned in Method 1, and its ¼- and ¹⁄₁₆-diluted liquid components in saline, each in 0.5 ml, were intraperitoneally administered to mice (n=4) before the dark-period (light off on 19:30 with a 12-hour cycle, at room temperature of 25° C.), and the food intake of each mice was measured over time. The control was the group administered with saline. The data are expressed as mean value±standard deviation. Determination of significant difference among each group was carried out by One-way analysis of variance (ANOVA).

4. Fractionation•isolation of constituents of the undiluted solution of liquid component based on molecular weight: A molecular weight cut-off membrane was employed in fractionating components showing approximately ½ of molecular weight, on the basis of a predicted molecular weight of nesfatin-1 (molecular weight of human nesfatin-1, 9,695 daltons) as the example of residual components. Accordingly, Centriprep 3K (supplied by Merck Millipore) of a molecular weight cut-off filter device (centrifugal filter device), which has a membrane material with molecular weight cut-off of 3,000 daltons, was used. The constituents contained in the undiluted solution of liquid component obtained as mentioned in Method 1 were fractionated into two kinds of liquid components; one component, containing nesfatin-1, showing a molecular weight of 3,000 daltons or more (the same meaning is applied to >3,000 component), and the other component showing a low molecular weight of 3,000 daltons or less (the same meaning is applied to <3,000 component). To obtain two different liquid components, the undiluted solution of liquid component was centrifuged at 3,600 rpm for 120 minutes using the above molecular weight cut-off filter device. The following centrifugation at 3,600 rpm for 60 minutes was carried out to fractionate and collect the filtrated liquid that was passed through the filter. To determine the fractionation efficiencies of the molecular weight cut-off filter device, using a spectrophotometer based on UV absorption method (wavelength 280 nm), the protein concentrations were measured in the undiluted solution of liquid component and the residual liquid component containing the >3,000 component. In addition, the concentrations of potassium (molecular weight, 39 daltons) were measured by ion electrode selection method in the undiluted solution of liquid component, the residual liquid containing the >3,000 component, and the filtrated liquid containing the <3,000 component. The concentrations of nesfatin-1 were measured by using the nesfatin-1 ELISA kit, as mentioned in Method 2. Furthermore, the amino acids in the undiluted solution of liquid component were measured by an automatic amino acid analyzing method.

5. Appetite-suppressing effect-2: Determination was made to clarify whether the residual liquid containing the >3,000 component obtained from the liquid component of Indian mulberry fruits showed a longer-period of appetite suppression than the undiluted solution of liquid component. The residual liquid containing the >3,000 component, which was obtained as mentioned in Method 4, and the undiluted solution of liquid component obtained as mentioned in Method 1, were intraperitoneally administered, each in an amount of 0.5 ml similar to the above Method 3, to mice (n=4) and the amounts of food intake in each of mice were measured over time. The control was the group administered with saline. The data are expressed as mean value±standard deviation. Determination of a significant difference among each group was carried out by One-way analysis of variance (ANOVA).

6. Appetite-suppressing effect-3: Determination was made to clarify whether the administration of the residual liquid containing the >3,000 component exhibited a stronger effect of appetite suppression than the undiluted solution of liquid component. The residual liquid containing the >3,000 component obtained as mentioned in Method 4, and its ¼- and ¹⁄₁₆-diluted liquid components in saline, each in 0.5 ml, were intraperitoneallly administered to mice (n=4) as mentioned in Method 3, and the amounts of food intake in each of mice were measured over time. The control was a group administered with saline. The data are expressed as mean value±standard deviation. Determination of a significant difference among each group was carried out by One-way analysis of variance (ANOVA).

7. Appetite-suppressing effect-4: Determination was made to see whether the administration of the filtrated liquid containing the <3,000 component obtained from the liquid component of Indian mulberry fruits exhibited an appetite-suppressing activity. The filtrated liquid containing the <3,000 component obtained as mentioned in Method 4 and the undiluted solution of liquid component, each in 0.5 ml, were intraperitonelly administered to mice (n=4) as mentioned in Method 3, and the amounts of food intake in each of mice was measured over time. The control was the group administered with saline. The data are expressed as mean value±standard deviation. Determination of a significant difference among each group was carried out by One-way analysis of variance (ANOVA).

8. Preference effect relating to conditioned taste aversion: Appetite can be non-specifically suppressed by a certain kind of material, which induces vomiting, throwing-up, unpleasant feeling, or taste disorder. To define whether the appetite-suppressing effects induced by the undiluted solution of liquid component, the residual liquid containing the >3,000 component, and the filtrated liquid containing the <3,000 component were non-specific, a conditioned taste aversive test (a conditioned taste aversion preference test) was carried out in mice. For 5 days, each of mice was adapted to two bottles containing water, allowing to the drinking schedule of 2 hours per day (10:00 am to 12:00). On Day 6 of the test, each mice was allowed to drink water for 30 minutes followed by installation of 2 bottles added with saccharine solution (0.15%). Thereafter, saline, the liquid components or lithium chloride (molecular weight: 42.4 daltons) solution, each in an amount of 0.5 ml, was intraperitoneally administered to mice (n=5), and the conditions were set up as the aversion learning of the taste against saccharine solution. Subsequently, each of mice was subjected to drink for 90 minutes using 2 botties with water. On Day 7 of the test, the animals were subjected to drink for 2 hours using 2 bottles with water. On Day 8 of the test, the animals were allowed to drink for 30 minutes using 2 bottles with either water or saccharine solution, and the preference ratio for drinking of saccharine solution (the amounts of saccharine solution intake÷the amounts of entire water intake for 2 bottles) was calculated. The administered concentration of each liquid component was a dose exhibiting approximately ½-food suppression of the saline-injected group as followed; a ¼-dilution of the undiluted solution of liquid component obtained as mentioned in Method 1, a 1/16-dilution of the residual liquid containing the >3,000 component obtained as mentioned in Method 4, and the undiluted filtrated solution containing the <3,000 component. As a material of non-specific suppression, a lithium chloride solution was used at a dose of 3 nmo/kg of body weight. The control was the group administered with saline. The data are expressed as mean value±standard deviation. Determination of a significant difference among each group was carried out by One-way analysis of variance (ANOVA).

Results

1. Detection 1 of nesfatin-1 in the undiluted solution of liquid component: Many of the undiluted solutions of liquid component were used to detect nesfatin-1, and it was found for the first time that only the undiluted solution of liquid component of a fruit of Indian mulberry contained nesfatin-1 at relatively high concentrations. Another undiluted solutions of liquid component did not contain nesfatin-1. The fruit of Indian mulberry was a product obtained by fermentation over 3 months approximately. FIG. 1 shows the concentration dilution curve of the liquid component of a fruit of Indian mulberry, which was measured for nesfatin-1 using the nesfatin-1 ELISA kit. A strongly positive relationship ($r^2$=0.98257) was shown between each of diluted concentrations of the liquid component and a measured concentration of the standard of nesfatin-1, suggesting that the liquid component contained nesfatin-1 and nesfatin-1-like substances. In FIG. 1, the vertical axis represents nesfatin-1 concentrations (ng/ml) and the horizontal axis represents the diluted amounts of the liquid component of a fruit of Indian mulberry. In contrast, each ELISA kit specific to leptin or adiponectin could not detect leptin or adiponectin in the undiluted solution of liquid component of a fruit of Indian mulberry.

2. Measurement 2 of nesfatin-1 in the undiluted solution of liquid component: Six different kinds of the undiluted solutions of liquid component of Indian mulberry, which were supplied by six independent manufactured companies, were used to detect nesfatin-1 using the nesfatin-1 ELISA kit. The concentrations of nesfatin-1 were detected in all liquid components of Indian mulberry, the dose ranging from 1.04 to 61.30 ng/ml concentrations (average concentration, 12.8 ng/ml). In line of these results, the experiments of appetite-suppressing effect were carried out using the undiluted solution of liquid component of Indian mulberry.

Figure 2:
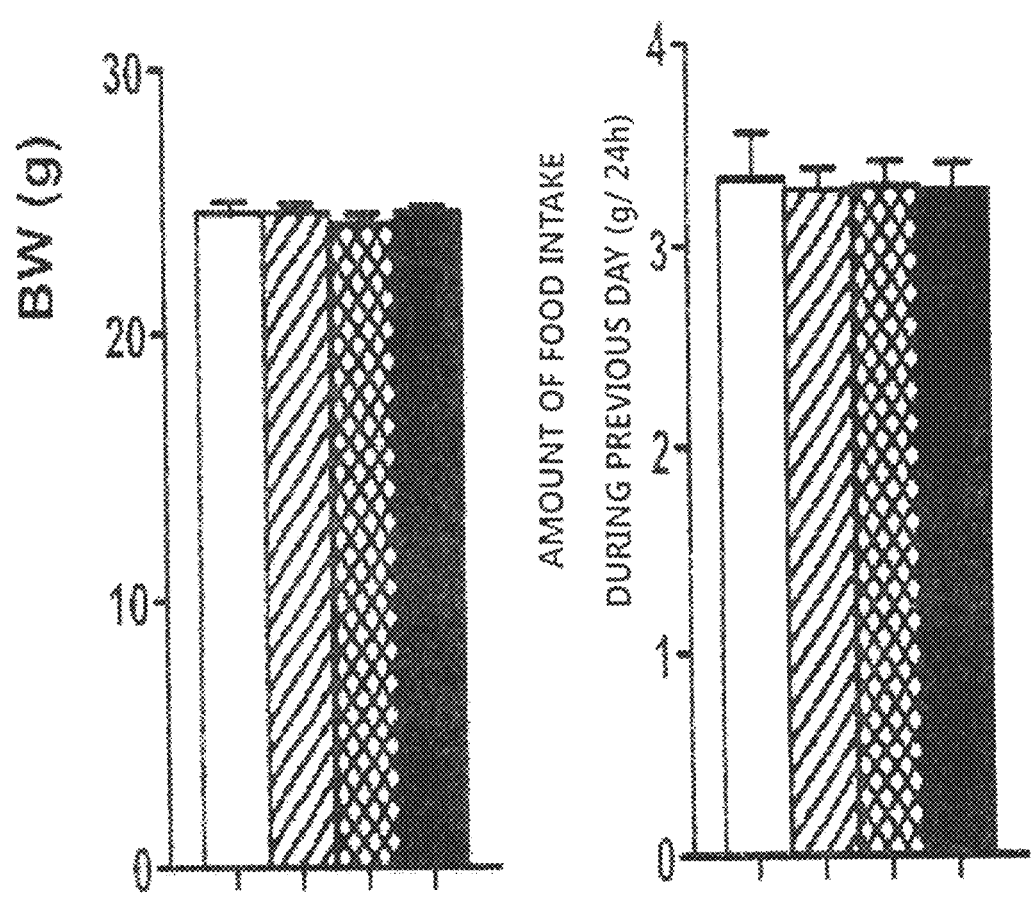
FIG. 2 shows the body weight and the amounts of daily food intake before experiment as shown in FIGS. 3 and 4.
Figure 3:
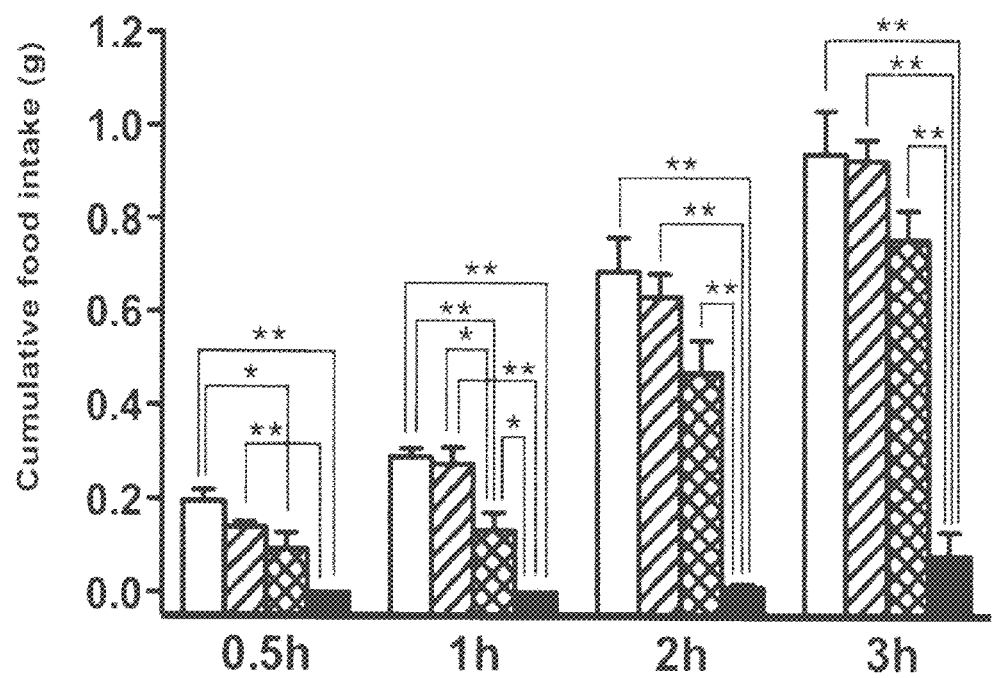
FIG. 3 shows the changes in the cumulative amounts of food intake in mice 0.5~3 hours after the administration of the diluted and undiluted solution of liquid component of Indian mulberry.
Figure 4:
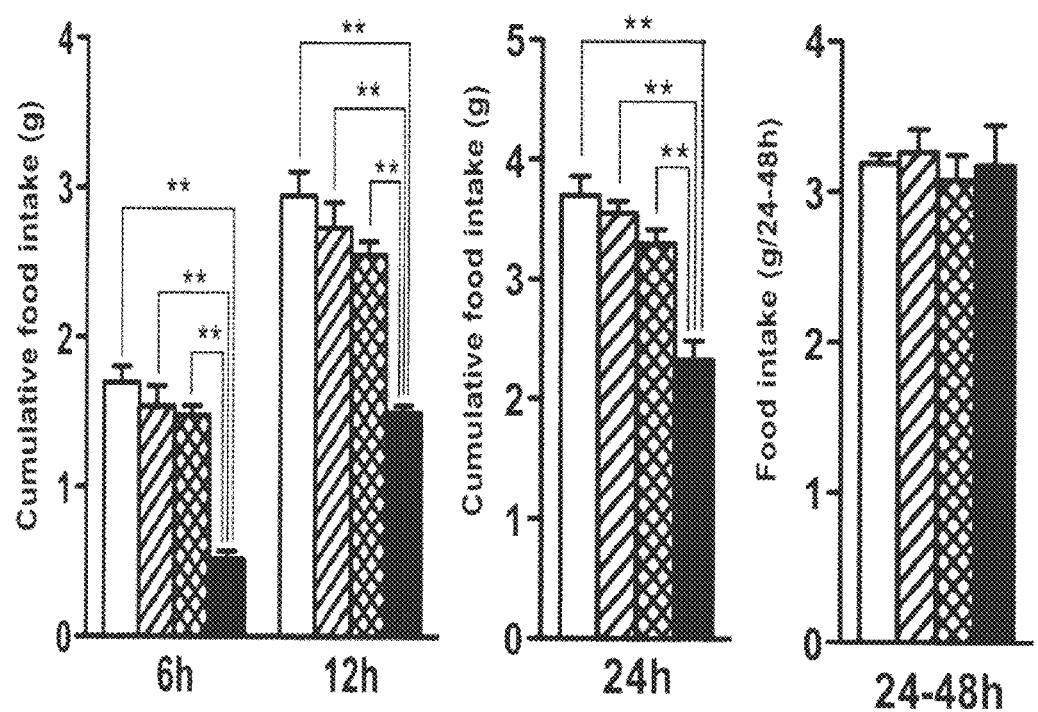
FIG. 4 shows the changes in the cumulative amounts of food intake in mice 6~48 hours after the administration of the diluted and undiluted solution of liquid component of Indian mulberry.

3. Appetite-suppressing effect-1: The undiluted solution of liquid component of Indian mulberry and its ¼- and 1/16-diluted solutions in saline were intraperitonelly administered to mice, and food intake of each of mice was measured. FIGS. 3 and 4 show that food intake was significantly suppressed by the administration of the solutions of liquid component of Indian mulberry in a dose-dependent manner. The concentration exhibiting 1/2- suppression of food intake during 1 to 2 hours after administration was a ¼-dillution. Furthermore, as illustrated in FIG. 4, suppression of food intake induced by the administration of the liquid component of Indian mulberry remained even after 12~24 hours of administration. However, 24~48 hours later, the suppression effect was not observed. These results indicate that the solution of liquid component of Indian mulberry suppressed appetite in a dose-dependent manner, and that its suppression effect was lost after 24 hours of administration. The body weight (BW) and 24 hour-food intake before experiment are illustrated in FIG. 2. The changes in the amounts of food intake after administration are illustrated in FIG. 3 and FIG. 4. In FIGS. 3 and 4, the vertical axis represents the cumulative amounts of food intake (g) and the horizontal axis indicates the time (h) after administration. The white column indicates the saline-injected group, the oblique-line column indicates the group administered with a 1/16-dilution, the striped column indicates the group administered with a ¼-dilution, and the black column indicates the group administered with the undiluted solution of liquid component. In FIGS. 3 and 4, * and ** Asterisks indicate significant differences ($P<0.05$ and $P<0.01$, respectively) compared with each of the comparable groups.

4. Fractionation•isolation based on molecular weight: The residual liquid containing the >3,000 component, which was obtained by fractionating the undiluted solution of liquid component of Indian mulberry using a molecular weight cut-off filter device, showed the protein concentrations of 189 to 219 mg/ml, whereas the undiluted solution of liquid component showed the protein concentrations of 50 to 58 mg/ml. The potassium concentrations were 46.6 mg in the undiluted solution of liquid component and were 4.1 mg in the residual liquid containing the >3,000 component, showing that the residual ratio of potassium was 8.8% on average. Accordingly, the potassium concentrations in the filtrated liquid containing the <3,000 component were 44.2 mg, showing that the filtrated ratio of potassium was calculated to be 94.8% on average. These results indicate that some components with low molecular weight such as potassium (molecular weight: 39 daltons) were included in the filtrated liquid containing the <3,000 component. Furthermore, the nesfatin-1 concentrations in the undiluted solution of liquid component ranged from 46 to 61 ng/ml (average, 55 ng/ml), whereas those in the residual liquid containing the >3,000 component ranged from 1,372 to 1,691 ng/ml (average, 1,504 ng/ml). The present results indicate that the nesfatin-1 concentration in the residual liquid containing the >3,000 component showed the 27-time high remaining ratio compared with the concentration in the undiluted solution of liquid component. Meanwhile, the nesfatin-1 concentrations in the filtrated liquid containing the <3,000 component ranged 0.5 to 10.3 ng/ml (average, 3.1 ng/ml), indicating that the filtrated concentration of nesfatin-1 was only 5.6% of the concentration of the undiluted solution of liquid component. Amino acids in the undiluted solution of liquid component showing a concentration of 1 mg/ml over were as follows; glutamic acid with molecular weight 147 daltons (1.89 mg/ml), asparaginic acid with 133 daltons (1.37 mg/ml), arginine with 174 daltons (1.07 mg/ml), and alanine with 89 daltons (1.02 mg/m1). Thus, it was suggested that most of the components showing low molecular weight were present in the filtrated liquid containing the <3,000 component.

Figure 5:
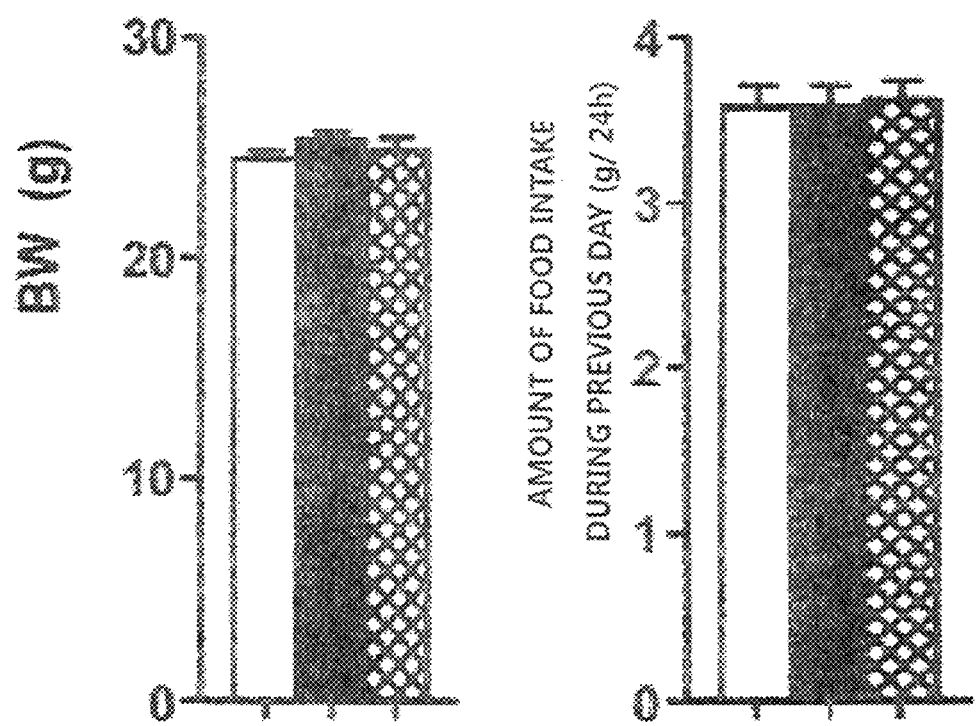
FIG. 5 shows the body weight and the amounts of daily food intake before experiment as shown in FIGS. 6 and 7.
Figure 6:
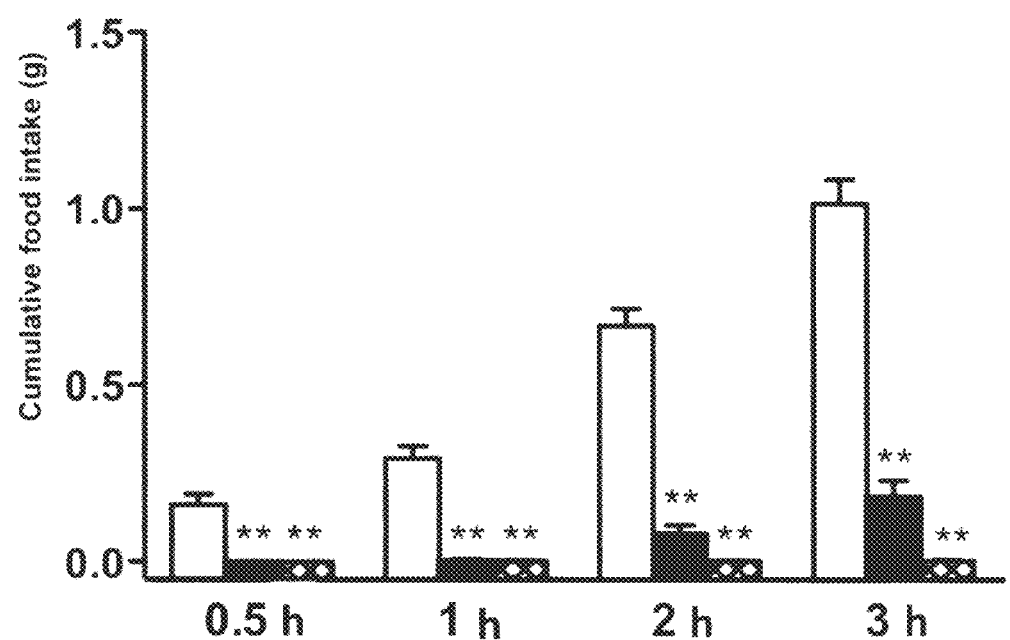
FIG. 6 shows the changes in the cumulative amounts of food intake in mice 0.5~3 hours after the administration of the undiluted solution of liquid component of Indian mulberry and the residual liquid containing the >3,000 component that was obtained using the molecular weight cut-off filter device.
Figure 7:
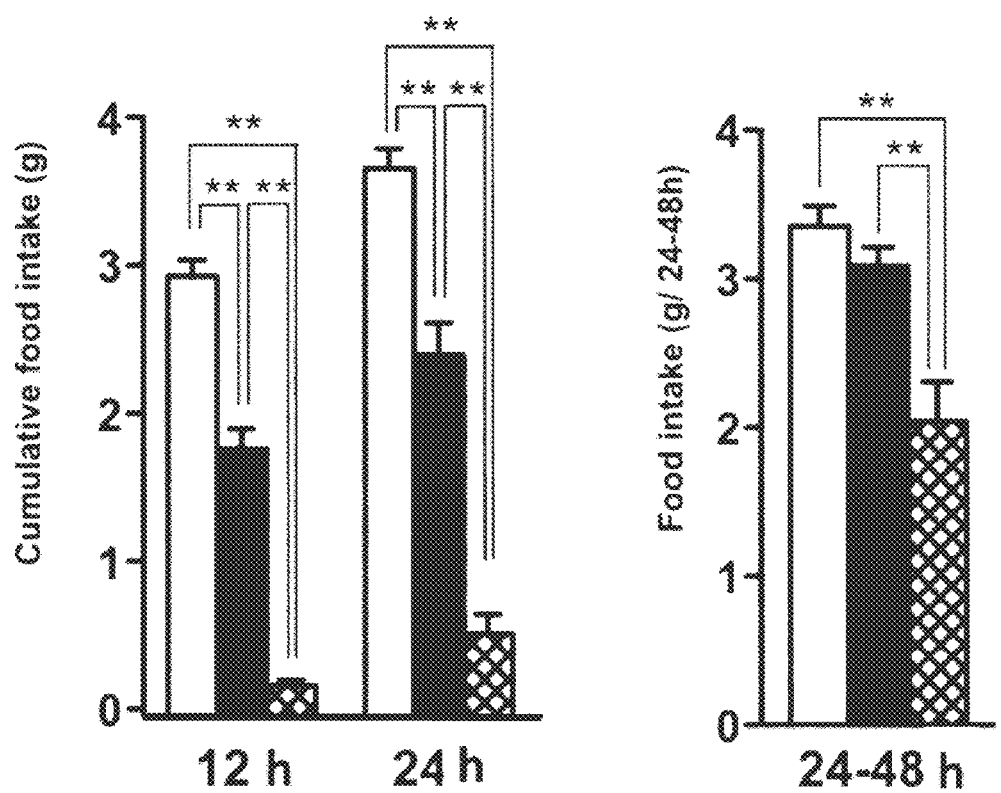
FIG. 7 shows the changes in the cumulative amounts of food intake in mice 12~48 hours after the administration of the undiluted solution of liquid component of Indian mulberry and the residual liquid containing the >3,000 component.

5. Appetite-suppressing effect-2 (long-term activity): The group administered with the residual liquid containing the >3,000 component exhibited a remarkable suppression of food intake as illustrated in FIGS. 6 and 7. Furthermore, as illustrated in FIG. 7, the activity of appetite suppression induced by the administration of the undiluted solution of liquid component was not observed after 24 hours of administration. In contrast, the activity of appetite suppression induced by the administration of the residual liquid containing the >3,000 component was significantly observed during a 24~48 hour-period after administration. These results indicate that the residual liquid containing the >3,000 component possessed a long-term activity of appetite suppression. The body weight (BW) and 24 hour-food intake before experiment are illustrated in FIG. 5. The changes in food intake over time after administration are illustrated in FIGS. 6 and 7. In FIGS. 6 and 7, the vertical axis represents the cumulative amounts of food intake (g) and the horizontal axis indicates the time (h) after administration. The white column indicates the saline-injected group, the black column indicates the group administered with the undiluted solution of liquid component, and the striped column indicates the group administered with the residual liquid containing the >3,000 component. and ** Asterisks indicate significant differences (p<0.05 and P<0.01. respectively) compared with the group administered with saline (FIG. 6) and each of the comparable groups (FIG. 7).

Figure 8:
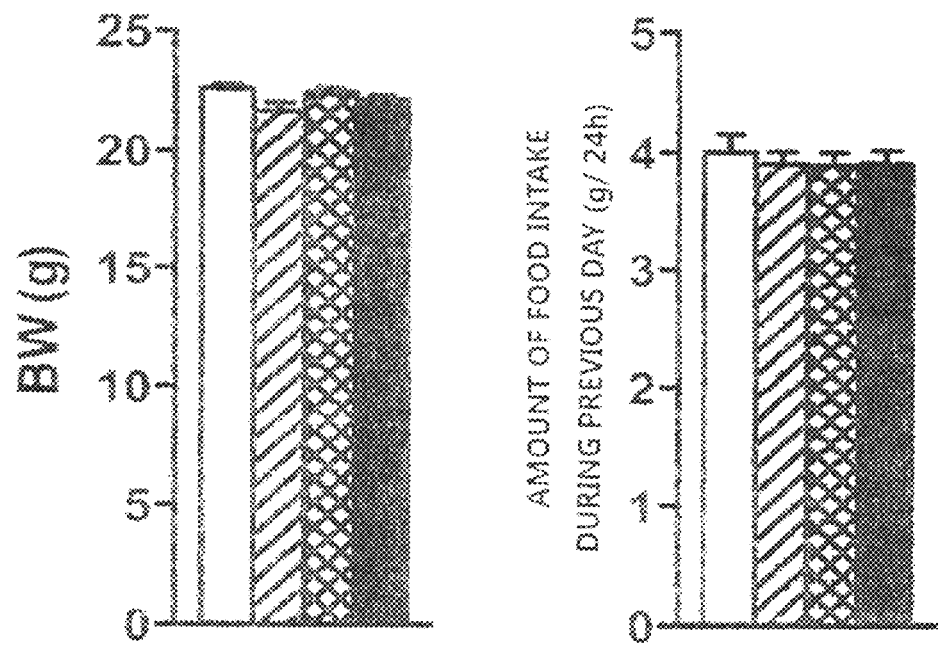
FIG. 8 shows the body weight and the amounts of daily food intake before experiment as shown in FIGS. 9 and 10.
Figure 9:
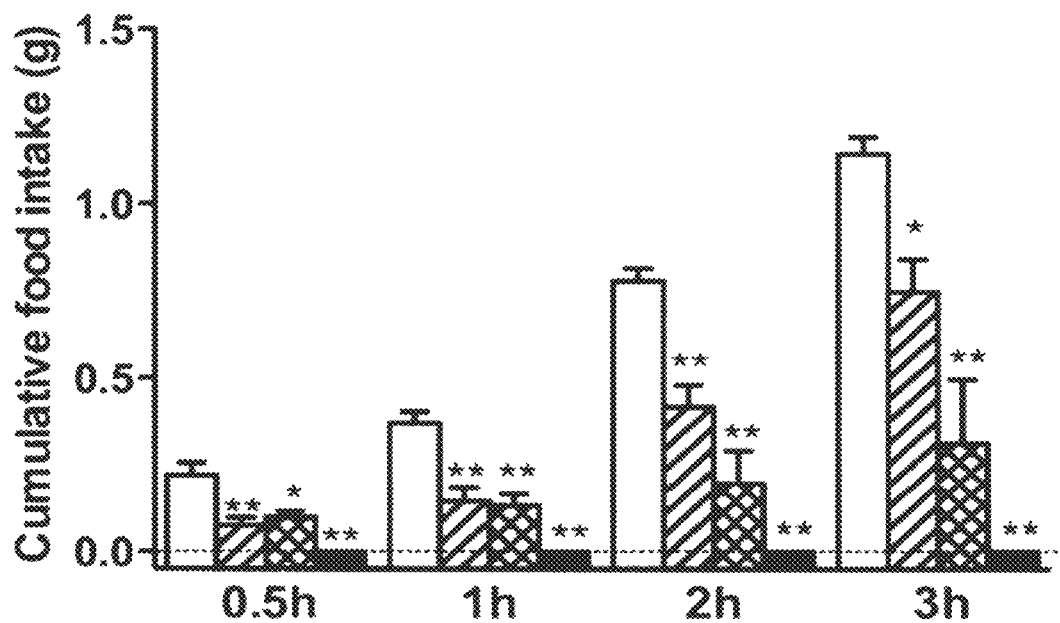
FIG. 9 shows the changes in the cumulative amounts of food intake in mice 0.5~3 hours after the administration of the diluted and undiluted solution of the residual liquid containing the >3,000 component.
Figure 10:
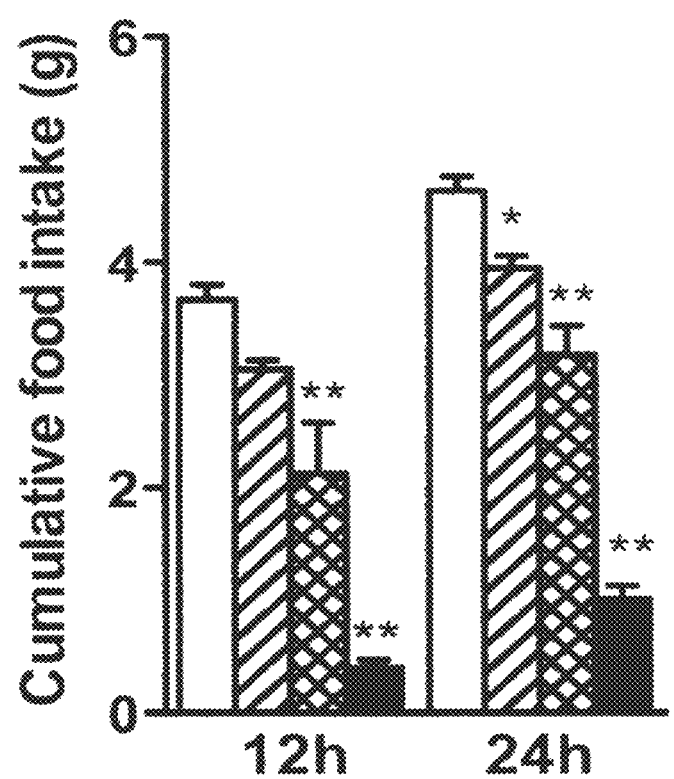
FIG. 10 shows the changes in the cumulative amounts of food intake in mice 12~24 hours after the administration of the diluted and undiluted solution of the residual liquid containing the >3,000 component.

6. Appetite-suppressing effect-3 (enhancing activity): The residual liquid containing the >3,000 component obtained from the liquid component of Indian mulberry, and its ¼- and ¹⁄₁₆-diluted solutions in saline were intraperitoneally administered to mice, and food intake of each of mice was measured. As shown in FIGS. 9 and 10, the administration of the residual liquid containing the >3,000 component suppressed food intake in a dose-dependent manner. The concentration showing ½-suppression of food intake during 1 to 2 hours after administration was found to be a ¹⁄₁₆-dilution, indicating that the appetite-suppressing effect was approximately 4 times stronger than the undiluted solution of liquid component. In addition, the appetite-suppressing activity remained until 24 hours after administration. These results clearly indicate that the residual liquid containing the >3,000 component possessed an enhancing activity with respect to appetite suppression. The body weight (BW) and 24 hour-food intake before experiment are illustrated in FIG. 8. The changes in the amount of food intake over time after administration are illustrated in FIGS. 9 and 10. In FIGS. 9 and 10, the vertical axis represents the cumulative food intake (g) and the horizontal axis indicates the time (h) after administration. The white column indicates the saline-injected group, the oblique-line column indicates the group administered with a ¹⁄₁₆-dilution, the striped column indicates the group administered with a ¼-dilution, and the black column indicates the group administered with the residual liquid containing the >3,000 component. * and ** Asterisks indicate significant differences (P<0.05 and P<0.01, respectively) compared with the saline-injected group.

Figure 11:
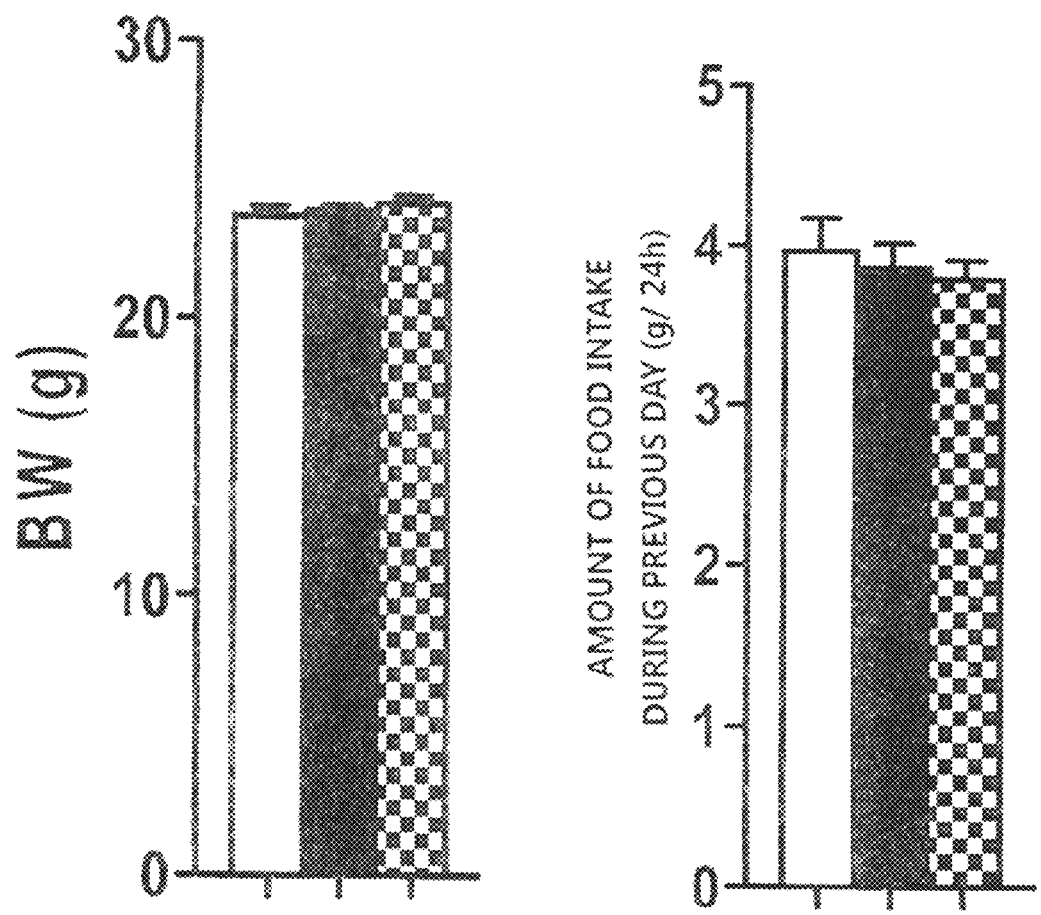
FIG. 11 shows the body weight and the amounts of daily food intake before experiment as shown in FIGS. 12 and 13.
Figure 12:
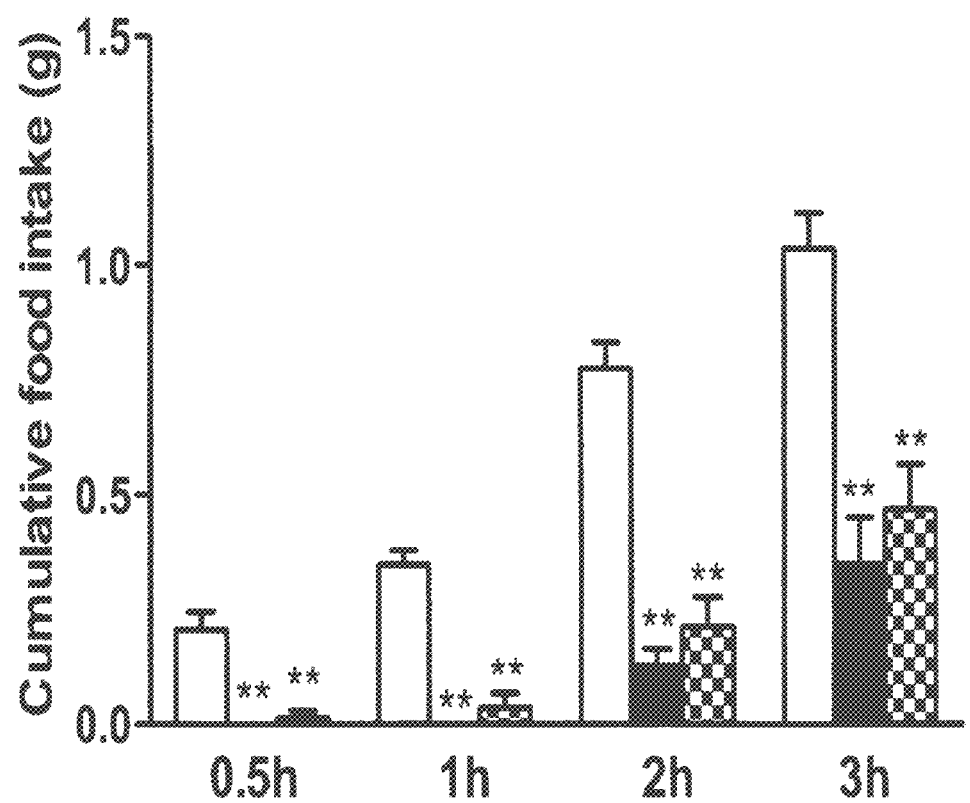
FIG. 12 shows the changes in the cumulative amounts of food intake in mice 0.5~3 hours after the administration of the undiluted solution of liquid component of Indian mulberry and the filtrated liquid containing the <3,000 component that was obtained using the molecular weight cut-off filter device.
Figure 13:
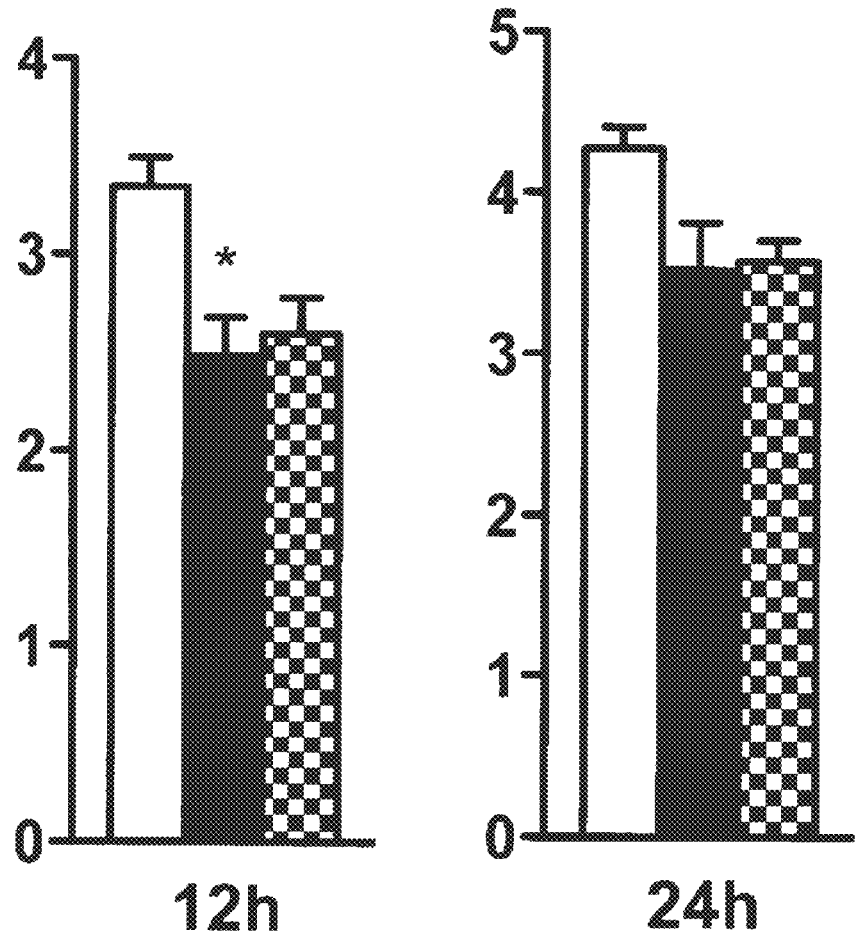
FIG. 13 shows the changes in the cumulative amounts of food intake in mice 12~24 hours after the administration of the undiluted solution of liquid component and the filtrated liquid containing the <3,000 component.

7. Appetite-suppressing effect-4 (component with low molecular weight): The group administered with the filtrated liquid containing the <3,000 component obtained from the liquid component of Indian mulberry exhibited significant appetite suppression as illustrated in FIGS. 12 and 13. Its suppressing activity was nearly equivalent to the activity observed in the group administered with the un diluted solution of liquid component. The filtered liquids contained components with low molecular weight such as potassium and amino acids. However, as illustrated in FIG. 13, the activity of appetite suppression induced by the filtrated liquid containing the <3,000 component was not observed after 24 hours of administration, indicating the activity similar to the undiluted solution of liquid component. These results imply that although the liquid component with low molecular weight of <3,000 daltons possessed a significant appetite-suppressing activity, this did not show an enhancing activity or a long-term activity. The body weight (BW) and 24 hour-food intake before experiment are illustrated in FIG. 11. The changes in food intake over time after administration are illustrated in FIGS. 12 and 13. The vertical axis represents the cumulative amounts of food intake (g) and the horizontal axis indicates the time (h) after administration. The white column indicates the saline-injected group, the black column indicates the group administered with the undiluted solution of liquid component, and the striped column indicates the group administered with the filtrated liquid containing the <3,000 component. * and ** Asterisks indicate significant differences (P<0.05 and P<0.01, respectively) compared with the saline-injected group.

Figure 14:
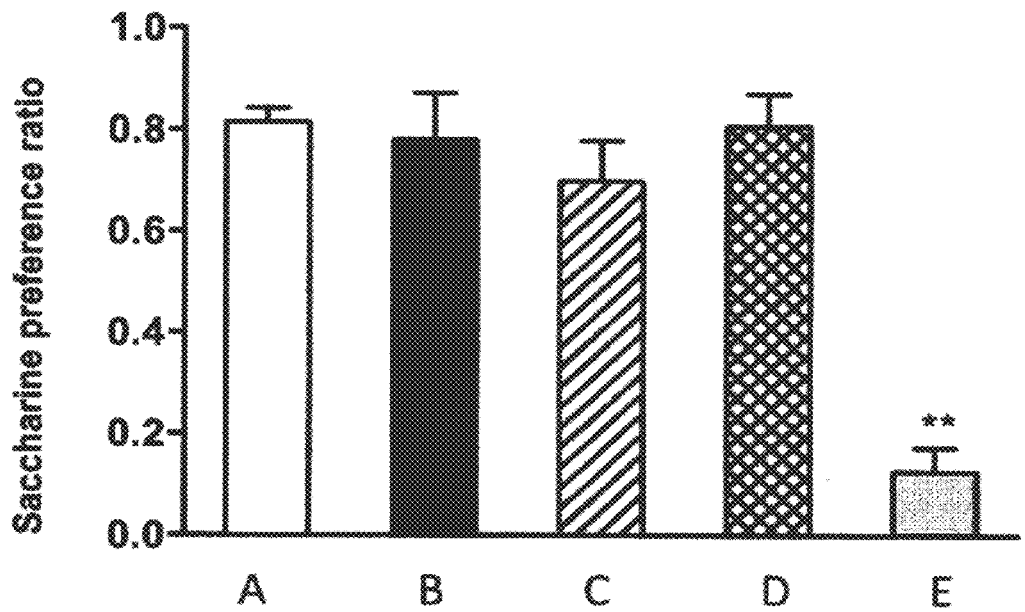
FIG. 14 shows the preference ratio for the in-take of saccharine solution in the conditioned mice after the administration of saline, the undiluted solution of liquid component of Indian mulberry, the residual liquid containing the >3,000 component, the filtrated liquid containing the <3,000 component, and lithium chloride.

8. Preference effect associated with conditioned taste aversion: As illustrated in FIG. 14, the administration of lithium chloride significantly suppressed the preference intake of saccharine solution. In contrast, the administration of the undiluted solution of liquid component, the residual liquid containing the >3,000 component, and the filtrated liquid containing the <3,000 component did not affect the preference intake of saccharine solution. These results indicate that the appetite-suppressing activities induced by the undiluted solution of liquid component, the residual liquid containing the >3,000 component, and the filtrated liquid containing the <3,000 component were not non-specific. The changes in preference intake of saccharine solution after the administration of each liquid are illustrated in FIG. 14. The vertical axis represents the preference ratio for saccharine intake. The white column indicates the saline-injected group (A), the black column indicates the group administered with the undiluted solution of liquid component (B), the oblique-line column indicates the group administered with the residual liquid containing the >3,000 component (C), the striped column indicates the group administered with the filtrated liquid containing the <3,000 component (D), and the grey column indicates the group administered with lithium chloride (E). ** Asterisk indicates a significant difference (P<0.01) compared with the saline-injected group.

Until nowadays, no data have been available with respect to appetite regulation induced by varying liquid food stuffs, which are commercially supplied in markets over a long-period of time, including the liquid component derived from a fruit of Indian mulberry. The present findings demonstrated for the first time that the liquid component of a fruit of Indian mulberry contained nesfatin-1, a satiety molecule, and that its liquid component exhibited the significant appetite-suppressing activity in a dose-dependent manner.

It was remarkably demonstrated for the first time that the residual liquid containing the >3,000 component showed the enhancing effect and the long-term acting effect on appetite suppression, compared with the undiluted solution of liquid component. In addition, this appetite-suppressing effect was not associated with a non-specific activity.

Furthermore, although the filtrated liquid containing the <3,000 component, which was prepared by means of the device of molecular weight cut-off filter, showed the significant appetite suppression, this filtrated liquid did not show any enhancing effect or long-term acting effect in suppressing appetite. Thus, the present findings showed for the first time that the filtrated liquid containing the <3,000 component, such as several amino acids derived from a fruit of Indian mulberry, possessed a appetite-suppressing effect without showing a non-specific activity.

Thus, as an appetite-suppressing composition, the present invention is very excellent.

Obviously, numerous modifications and variations of the present invention are possible in light of the above teachings. It is therefore to be understood that within the scope of the appended claims, the invention may be practiced otherwise than as specifically described herein.

What is claimed is:

1. A method for suppressing obesity or for suppressing the development of obesity, the method comprising:
    administering an appetite-suppressing composition to a subject in need thereof,
    wherein the appetite-suppressing composition comprises a filtrated liquid fraction obtained by fractionating, using a molecular cut-off filter device, an undiluted solution of a liquid component extracted from a fruit of Indian mulberry (*Morinda citrifolia*), wherein the filtrated fraction has a molecular weight of constituents of 3,000 daltons or less and comprises glutamic acid, asparaginic acid, arginine, and alanine, wherein a nesfatin-1 concentration in the filtrated fraction is from 0.5 to 10.3 ng/ml, and wherein the appetite suppressing activity of the filtrated fraction is not enhanced compare to an appetite suppressing activity of the undiluted solution of the liquid component extracted, and
    the administering is oral, via injection, via a suppository or transdermal,
    wherein the undiluted solution of a liquid component is a supernatant obtained upon centrifugation of the liquid component.

2. The method of claim 1, wherein the appetite-suppressing composition further comprises at least one agent selected from the group consisting of a solvent, an oil, an emulsifying agent, a preservative, a fragrance, a stabilizing agent, a coloring agent, an anti-oxidizing agent, a moisturizing agent, and a thickening agent.

* * * * *